United States Patent
Qin et al.

(10) Patent No.: US 8,623,328 B2
(45) Date of Patent: *Jan. 7, 2014

(54) USE OF DKK-1 PROTEIN IN THE CANCER DIAGNOSIS

(75) Inventors: Wenxin Qin, Shanghai (CN); Haitao Zhang, Shanghai (CN); Yanjun Yu, Shanghai (CN); Haiyan You, Shanghai (CN); Shengli Yang, Shanghai (CN); Jianren Gu, Shanghai (CN); Gang Huang, Shanghai (CN); Shile Sheng, Shanghai (CA); Tao Chen, Shanghai (CN)

(73) Assignee: Shanghai Cancer Institute, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/570,617

(22) Filed: Aug. 9, 2012

(65) Prior Publication Data

US 2012/0329669 A1 Dec. 27, 2012

Related U.S. Application Data

(63) Continuation of application No. 12/268,532, filed on Nov. 11, 2008, now Pat. No. 8,263,039, which is a continuation of application No. PCT/CN2006/000382, filed on Mar. 13, 2006.

(51) Int. Cl.
  *A61B 5/00* (2006.01)
  *A61B 8/00* (2006.01)
  *A61B 10/00* (2006.01)

(52) U.S. Cl.
  USPC ......... 424/9.6; 424/1.11; 424/1.49; 424/1.73; 424/1.89; 424/9.1; 424/1.65

(58) Field of Classification Search
  USPC ........... 424/1.11, 1.49, 1.65, 1.69, 1.73, 1.81, 424/1.85, 1.89, 9.1, 9.3, 9.4, 9.5, 9.6, 9.7, 424/9.8, 178.1; 514/1, 1.1, 18.9, 19.2, 19.3; 530/300, 350, 387.1, 387.2, 387.3, 530/387.7, 388.1, 300.15, 388.8, 391.1, 530/391.3
  See application file for complete search history.

(56) References Cited

U.S. PATENT DOCUMENTS

| 4,331,647 A | 5/1982 | Goldenberg |
| 7,057,017 B2 | 6/2006 | McCarthy |

FOREIGN PATENT DOCUMENTS

| CN | 1963511 | * | 5/2007 |
| JP | 2006-207844 | | 2/2005 |
| WO | 2005/002047 | | 8/2000 |
| WO | 2004/053063 | | 6/2004 |
| WO | 2005/033343 | | 4/2005 |

OTHER PUBLICATIONS

Boyden et al., "High bone density due to a mutation in LDL-receptor-related protein 5" N Engl J Med, 2002; 346(20): 1513-1521.
Fedi P., et al., "Isolation and biochemical characterization of the human Dkk-1 homologue, a novel inhibitor of mammalian Wnt signaling" (J Biol Chem, 1999; 274(27):19465-72).
Glinka et al. "Dickkopf-1 is a member of a new family of secreted proteins and functions in head induction" Nature 1998;391(6665):357-362.
Mikheev et al. "A functional genomics approach for the identification of putative tumor suppressor genes: Dickkopf-1 as suppressor of HeLa cell transformation" (Carcinogenesis, 2004: 25(1):47-59).
NCBI Accession No. NP 571078 Retrieved online from NCBI Sequence Viewer v2.0 Jan. 2009 3 pages.
Ohnaka et al., "Glucocorticoid enhances the expression of dockkopf-1 in human osteoblasts: novel mechanism of glucocorticoid-induced osteoporosis" Biochemical and Biophysical Research Communications 318 (2004) 259-64.
Sambrook et al., "Molecular cloning: a laboratory manual" Cold Spring Harbor Laboratory 1989. Title page and table of contents.
Tian et al. "The role of the Wnt-signaling antagonist DKK1 in the development of osteolytic lesions in multiple myeloma" N Engl J Med, 2003;349(26):2483-2494.
Wirths O et al.: Overexpression human Dickkpf-1, an antogonist of wingless/WNT signaling, in human hepatoblasomas and Wilms' tumors (Lab Invest, 2003; 83(3): 429-434).

* cited by examiner

*Primary Examiner* — D L Jones
(74) *Attorney, Agent, or Firm* — Hamre, Schumann, Mueller & Larson, P.C.

(57) ABSTRACT

Use of DKK-1 protein or the nucleic acid sequence in preparation of cancer diagnostic agents or kits, method to detect liver cancer with the monoclonal antibody thereof, the kit comprising anti-DKK-1 antibody or protein specific nucleic acid probes, together with a label, and method to detecting specific DKK-1 protein expression are disclosed.

8 Claims, 4 Drawing Sheets

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
gacccaggct tgcaaagtga cggt                                    24

<210> SEQ ID NO 2
<211> LENGTH: 27
<212> TYPE: DNA

-continued

```
<213> ORGANISM: Artificial Sequence
<220> FEATURE:
<223> OTHER INFORMATION: primer

<400> SEQUENCE: 2
aggagttcac tgcatttgga tagctgg                                             27
```

USE OF DKK-1 PROTEIN IN THE CANCER DIAGNOSIS

CROSS-REFERENCE TO RELATED APPLICATION(S)

This application is a continuation of U.S. Ser. No. 12/268,532 filed Nov. 11, 2008, which is a continuation of PCT application No. PCT/CN2006/000382 filed Mar. 13, 2006, which applications are incorporated herein by reference.

TECHNICAL FIELD

The present invention relates to molecular biology, particularly genetic diagnosis. Specifically, the present invention relates to the use of DKK-1 protein in diagnosis of cancer.

BACKGROUND ART

In 1998, Glinka A. et. al. published a research article in Nature (Nature, 1998; 391(6665):357-362), which claims that they have found a new secretory protein in the research work of the embryo development of *Xenopus laevis*, which is called dickkopf-1 (dkk-1). Their research confirms that dkk-1 is the inhibitory factor of Wnt signaling pathway and is "inducer" formed in the "head induction" during the embryonic development of *Xenopus laevis*. Later, in 1999, Fedi P., et. al. (J Biol Chem, 1999; 274(27):19465-72) isolated human homologous gene of dkk-1 from human leiomyosarcoma cell SK-LMS-1 and the corresponding cDNA library by conditioned chromatogram and PCR. The mRNA transcript is about 2 kb, encoding 266 amino acids. Since then, the scientists for the first time reveal the molecular mechanism of DKK-1 as Wnt signaling pathway inhibitor through near 5 years of research work.

During the research work of the function and action mechanism of DKK-1, the scientists also notice that DKK-1 is relevant to certain human diseases, such as osteoporosis (Biochem Biophys Res Commun, 2004; 318(1):259-264. N Engl J Med, 2002; 346(20):1513-1521), bone damage caused by multiple myeloma (N Engl J Med, 2003; 349(26):2483-2494) and other human malignancy. For example, Mikheev A M et. al. (Carcinogenesis, 2004; 25(1):47-59) established 2 non-tumorigenic revertant cell lines with human cervical cancer Hela cell line, and found by cDNA chip that DKK-1 is highly expressed in the above 2 non-tumorigenic revertant cell lines and that lack of DKK-1 expression is necessary for Hela tumogenicity. Therefore, DKK-1 is deemed as a candidate cancer inhibitory gene. Furthermore, Wirths O et. al. (Lab Invest, 2003; 83(3):429-434) use "suppression subtractive hybridization approach" to find that DKK-1 is highly expressed in children hepatoblastoma and Wilms' tumor. The result shows that 26 out of 32 children hepatoblastomas highly express DKK-1 (26/32, 81%), 5 out of 6 Wilms' tumors highly express DKK-1 (5/6, 83%). However, only 2 out of 20 liver cancer patients highly express DKK-1 (2/20, 10%), and 1 out of 5 medulloblastoma cell lines highly express DKK-1 (1/5, 20%). There is no DKK-1 expression in malignant gliomas and breast cancers.

Therefore, there is urgent need for the precise and specific diagnosis of particular cancers.

SUMMARY OF THE INVENTION

Therefore, the object of the present invention is to provide diagnosis kit for precise diagnosis of selected cancer, the use of the DKK-1 diagnosis kit, and the methods of in vitro detection of the expression amount thereof.

In one aspect of the present invention, it provides a cancer diagnosis kit, wherein the said cancer selected from liver cancer, lung cancer, breast cancer and glioma, comprising containers with anti-DKK-1 antibody therein. In one preferred embodiment of the present aspect, the anti-DKK-1 antibody is conjugated to detectable moieties. In a more preferred embodiment, the detectable moieties are selected from chromophore, chemical luminescent group, fluorophore, or isotopes.

In the second aspect of the present invention, it provides a cancer diagnosis kit, wherein the said cancer is selected from liver cancer, lung cancer, breast cancer and glioma, comprising containers with DKK-1 protein specific nucleic acid probe therein. In a further preferred embodiment of the present aspect, the probe is conjugated to detectable moieties. In a more preferred embodiment, the detectable moieties are selected from chromophore, chemical luminescent group, fluorophore, or isotopes.

In the third aspect of the present invention, it provides the use of DKK-1 protein or the nucleic acid sequence thereof in preparation of cancer diagnostic agent or kit, wherein the cancer selected from liver cancer, lung cancer, breast cancer and glioma. In one preferred embodiment of the present aspect, the cancer diagnostic agent is anti-DKK-1 protein specific antibody or DKK-1 protein specific nucleic acid probe.

In the fourth aspect, it provides a method for in vitro detecting specific DKK-1 protein expression, comprising:

reacting anti-DKK-1 protein specific antibody or DKK-1 specific nucleic acid probe with cell sample, with normal cell as control;

comparing the binding amount of the antibody or probe, wherein the increased amount over the control indicates the cancer cell, the lower or equal amount indicates normal cell.

In one preferred embodiment of the present aspect, the binding amount is measured by detecting the detectable moiety conjugated to the probe or antibody.

In the fifth aspect, it provides a method for detecting liver cancer, comprising the following step:

a) administering to an animal the anti-DKK-1 monoclonal antibody conjugated to radionuclide;

b) detecting the gathering of anti-DKK-1 monoclonal antibody in vivo;

c) the said gathering indicates the presence of liver cancer.

In one preferred embodiment, the radionuclide is $^{133}$I. In another preferred embodiment, the animal is human.

DETAILED EMBODIMENT OF THE INVENTION

Figure 1:
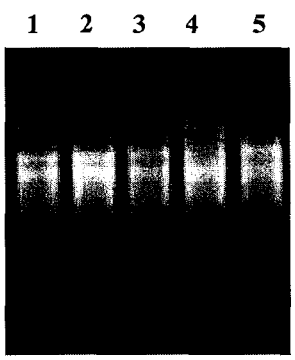
FIG. 1 indicates the electrophoresis map of cRNA labeled by biotin. 1-5 are sample numbers.

The inventors compare difference of the gene expression profile of the liver cancer and the corresponding liver tissue adjacent to the cancer by genechip technology, and discover that it is contrary to the result of Wirths O et. al. (Lab Invest, 2003; 83(3):429-434) that DKK-1 only expresses in a few liver cancer patients (2/20, 10%). In the liver cancer patients analyzed and confirmed by the inventors, 7 out of 12 have DKK-1 high expression in the liver cancer tissue (7/12, 58%), obviously higher than the result reported by Wirths O for the liver cancer. Therefore, using ELISA, it is for the first time that the DKK-1 amount in the serum of liver cancer patients is tested, which indicates that it highly expresses and secretes DKK-1. Based on this, it can be used in clinic diagnosis and therapy of liver cancer.

As used herein, the term "DKK-1" is a new secretory protein found in the research of *Xenopus laevis* embryo development, which is named dickkopf-1 (dkk-1). The sequence of the protein can be found by NCBI accession number NP 571078. The DKK-1 protein herein comprises the complete amino acid sequence, the secretory protein, the mutant, and the functional active fragments. It should be understood that when encoding the same amino acid, the nucleotide replacement in the codon is acceptable. Further to be understood is that in case of conservative amino acid replacement produced by nucleotide substitution, the replacement of nucleotide is acceptable.

When the amino acid fragments of DKK-1 are obtained, encoding nucleic acid sequences can be constructed, and the specific probes can be designed according to the nucleotide sequence. The full-length nucleotide sequence or the fragment thereof can be produced by PCR amplification, recombination or artificial synthesis. For PCR amplification, primers can be designed by the disclosed nucleotide sequences, particularly the open reading frame sequence, using commercially available cDNA library or cDNA library prepared by the common technology known by the skilled in the art to amplify the sequence. When the sequence is long, 2 or more times of PCR amplification is needed, then to link the fragments produced each time in right sequence.

Once relevant sequence is obtained, recombination method can be used to massive produce the sequence, which commonly relates to clone the sequence into a vector, transfer into cell, and then isolate from the propagated host cells by common method to obtain the sequence.

Furthermore, artificial synthesis can be used to synthesize the sequence, especially when the fragment is relative short. Usually fragments with long sequences can be obtained by first synthesizing multiple small fragments and then linking them.

At present, the DNA sequence encoding the protein (or the fragments and derivatives) of the present invention can be produced by chemical synthesis. Then, the said DNA sequence can be introduced into any known DNA molecules (or vectors) and the cells in the art.

By common recombination DNA technology, the present polynucleotide sequence can be used to express or produce recombinant DKK-1 polypeptide. It usually comprises the following steps:

(1) Transform or transduct the suitable host cell by the present polynucleotide (or mutant) encoding human DKK-1 polypeptide, or recombinant expression vector comprising the said polynucleotide;
(2) Culturing host cell in suitable culture medium;
(3) Isolating and purifying the protein from the culture medium or the cells.

In the present invention, DKK-1 polynucleotide sequence can be inserted into recombinant expression vectors. Generally any vectors and plasmids can be used as long as they can replicate and be stable in the host. One important character of the expression vector is that it usually comprises the replicate origin, promoter, marker gene and translation control element.

Methods well known by the skilled in the art can be used to construct the expression vectors comprising DKK-1 coding DNA sequence and suitable transcription/translation control signal. These methods include in vitro recombinant DNA technology, DNA synthesis technology, in vivo recombination technology, etc. The said DNA sequence can be effectively linked to suitable promoter in the expression vector to guide mRNA synthesis. Expression vectors also include ribosome binding site for starting the translation and the transcription terminators.

Furthermore, expression vector preferably comprises one or more selective marker genes to provide the phenotypes which can be used to select the transformed host cell, for example, dihydrofolate reductase, neomycin resistance and green fluorescent protein (GFP) for eukaryote, or tetracycline or ampicillin resistance for *E. coli*.

The vectors comprising the above suitable DNA sequences and suitable promoters or regulating sequences can be used to transform suitable host cells to express proteins.

The host cells can be prokaryotic cells, for example bacteria cells; or lower eukaryotic cells, for example yeast cells; or higher eukaryotic cells, for example mammalian cells. The representative examples are *E. coli*, bacteria cells of *Streptomyces*; fungal cells for example yeast; plant cells, insect cells; animal cells.

Transforming host cells with recombinant DNA can perform with common technology well-known by the skilled in the art. When the host is prokaryotes for example *E. coli*, the competent cells that can absorb the DNA can be obtained after the logarithmic growth phase, processed by $CaCl_2$ method, and the steps used are known in the art. The other method is to use $MgCl_2$. If necessary, transforming can also use electroporation. When the hosts are eukaryotes, following DNA transfection method can be selected: calcium phosphate coprecipitation, normal mechanical methods such as microinjection, electroporation, liposome packing, etc.

The obtained transformant can be cultured with common method to express the polypeptide encoded by the present genes. According to the host cell used, the medium used in the cultivation can be selected from all kinds of regular mediums. The cultivation can be done under conditions suitable for the growth of the host cells. When the host cells grow into the desired cell density, suitable methods can be used to induce selected promoter (for example by temperature shift or chemical induction) and the cell can be cultured for some time more.

The recombinant polypeptides from the above method can be expressed in the cell, on the cell membrane, or secreted outside the cell. If necessary, recombinant proteins can be isolated and purified by various isolation methods utilizing its physical, chemical or other characters. These methods are well known by the skilled in the art. Examples of these method include, but not limited to, regular renaturation process, protein precipitator treatment (salt out), centrifugation, osmotic breaking-up of the bacteria, ultrasonication, ultracentrifugation, molecular sieve chromatography (gel filtration), adsorption chromatography, ion exchange chromatography, high performance liquid phase chromatography (HPLC) and other liquid phase chromatography, and the combinations thereof.

After obtaining the nucleic acid sequence, specific nucleic acid probe can be designed according to the sequence. Methods for designing the probes are common in the art, See Sambrook et. al., Molecular Cloning, A Laboratory Mannual, Second edition, Cold Spring Harbor Laboratory, Cold Spring Harbor, 1989. The exemplary method for testing whether DKK-1 protein or nucleic acid exists in the biological samples comprises examining the biological sample of the subject, exposing the said biological sample to labeled nucleic acid probes that can hybrid with DKK-1 mRNA or genomic DNA. The nucleic acid probes can be for example human nucleic acid or part of it, for example of at least 15, 30, 50, or 100 nucleotides and the nucleic acid probes that can sufficiently hybrid with DKK-1 mRNA or genomic DNA. Other probes used in the present diagnosis assay are as mentioned herein.

Nucleic acid probes contact with the labeled and amplified sequences. The probes preferably are linked to chromophore, but can also be radioactive labeled. In another embodiment, the probes are linked to binding partner, for example antibody or biotin, or another binding partner with a detectable domain.

In the traditional methods, the detection can be realized by Southern blotting and hybridization with labeled probes. The technology of Southern blotting is well known by the skilled in the art (See Sambrook et. al., 1989). Common detections also include biochips, florescent imaging technology, and flow cytometry, etc.

In another expect, the present invention also includes the specific polyclonal antibodies and monoclonal antibodies, particular monoclonal antibodies, against polypeptides encoded by DKK-1 DNA or the fragments thereof. Herein, "specific" means that the antibody can bind with DKK-1 gene product or fragments thereof, preferably those antibodies that bind with DKK-1 gene product or fragment but do not recognize and bind other non-relevant antigen molecules. The present antibody can be prepared by any technologies known by the skilled in the art.

The present invention not only include the complete monoclonal or polyclonal antibodies, but also the antibody fragments that have immune activity, for example Fab' or (Fab)$_2$ fragments, antibody heavy chain, antibody light chain, single chain Fv molecules modified by genetic engineering, or chimeric antibodies.

Anti-DKK-1 antibody can be used in immunohistochemistry to detect the DKK-1 protein in the biopsy samples.

The direct detection of DKK-1 in blood or urine sample can be observation index for tumor assistant diagnosis and prognosis, and can also be the basis of tumor early diagnosis.

Antibodies can be detected by ELISA, Western blotting, or linked with detecting groups, which can be detected by chemiluminescence, and isotopic tracing.

The present invention also includes kit to perform any method described herein. In one non-limiting example, the kit can include one or more of the reagents with suitable forms of containers. The kit can also comprise reagents and labels for RNA isolation and purification of the RNA in the amplified cells.

The components of the kit can be packed in aqueous medium or in lyophilized form. The suitable containers in the kit usually at least include one vial, tube, flask, bottle, syringe or other containers, which can have one components, and preferably suitably parted. When there is more than one component in the kit, the kit will usually have second, third and other additional containers, which can separately hold additional components. However, different combination of the components can be included in one vial. The present invention usually includes one container to hold the reactants, which is sealed for commercial distribution. The said container can include die-cast or blow molded plastic containers, in which the necessary vial can be kept.

The present invention is further described hereinafter with particular examples. It should be understood that these examples are just used to explain the invention, not to limit the scope of the invention. The experimental methods without particular conditions in the following examples usually use the regular conditions, for example those described in Sambrook et. al., Molecular Cloning, A Laboratory Mannual, Cold Spring Harbor Laboratory Press, New York, 1989, or as suggested by the producers.

Example 1

Collection of the Tumor Tissue and Non-Cancerous Liver Tissue Sample from Liver Cancer Patients 12 samples of the tumor tissues from human hepatocellular carcinomas (T) and non-cancerous liver tissues (N) were collected from the liver cancer patients from Shanghai, Guangxi, Qidong Jiangsu, and Hangzhou in China. In these samples, 1 from Shanghai (D129), 2 from Guangxi (G65 and G319), 4 from Qidong Jiangsu (Q130, Q135, Q142, Q162), and 5 from Hangzhou (HK114, HK120, HK121, HK164, HK165). After operation, the tissue samples were immediately frozen in liquid nitrogen, and then stored in −80° C. ultra low temperature refrigerator.

Example 2

Isolation of RNA 1) 1 g tissue sample was triturated in liquid nitrogen into powder, then immediately added into 10 ml TRIZOL (Invitrogen, Cat 15596-026) to homogenate. Left under room temperature (RT) for 10-15 minutes.

2) 2 ml chloroform was added and shaked vigorously 15 s. Left under RT for 2-3 mins, centrifugated at 10,000 g at 4° C. for 15 mins.

3) Supernatant was collected, into which the same volume of isopropanol was added. Left under RT for 2-3 mins, and then centrifugated at 10,000 g at 4° C. for 15 mins.

4) Supernatant was discarded, 6 ml 75% ethanol was added to rinse the pellet. Centrifugated at 10,000 g at 4° C. for 15 mins.

5) The RNA pellet was slightly dried and solved in DEPC water.

6) The above crude total RNA sample was purified by RNeasy Mini Kit (Qiagen, Cat 74104) following the purification steps provided by the instruction of the said kit from Qiagen. The purified DNA was kept under −70° C. for next use.

Example 3 cDNA Chip Hybridization Assay

1) UV Quantification and Detection:

UV spectrophotometer was used to detect the amount of the RNA. 1 Absorbance Unit (OD) at 260 nm equals to about 40 μg/ml RNA. According to the OD at 260 nm and 280 nm, the purity of the RNA is detected. The ratio of $OD_{260\ nm}/OD_{280\ nm}$ of rather pure RNA should be near 2.0 (preferable ratio should be 1.9-2.1).

2) cDNA Synthesis and Purification:

Synthesis of the first chain cDNA. Total RNA 5 μg was added with RNAse-free water into total volume 20 μl. T7-$(dT)_{24}$ primer 1 μl (100 pmol/μl) was added and incubated at 70° C. for 10 min, then placed on ice for at least 2 min and centrifuged. Then 5× first chain cDNA synthesis buffer 4 μl, DTT (0.1M) 2 μl and dNTP (10 mM) 1 μl were added, mixed thoroughly, and incubated at 42° C. for 2 min. Then SuperScript II RT (200 u/μl) 1 μl (5-8 μg starting RNA) was added, mixed thoroughly and incubated at 42° C. for 1 hour.

Synthesis of the second chain cDNA. The above RT-PCR synthesized first chain cDNA product was left on the ice, and the following agents are added: RNAse-Free water 92 μl, 5× second chain cDNA synthesis buffer 30 μl, DTT (10 mM) 3 μl, *E. coli* DNA ligase (10 u/μl) 1 μl, *E. coli* DNA polymerase (10 u/μl) 4 μl, *E. coli* RNase H (10 u/μl) 0.2 μl. The reactants were mixed thoroughly and reacted at 16° C. for 2 hours. Then T4 DNA polymerase 3.3 μl was added, mixed thoroughly, and reacted at 16° C. for 5 min. Then 10 μl EDTA (0.5M) was added, mixed thoroughly to end the reaction. The product was stored at −20° C.

cDNA purification. The above cDNA was purified by Eppendorf PLG (Phase Lock Gel), PLG tubes were centrifuged at 12,000 g for 30 s. Phenol:Chloroform:isopropanol (25:24:1) was added at 1:1 into the cDNA reaction product, shaken vigorously. All the liquid was transferred into PLG tubes without shake, centrifuged at 12,000 g for 2 min at RT. The supernatant was aspired into a new centrifuge tube, and 0.5 volume of ammonium acetate (7.5M, pH8.0) and 2.5 volume of pre-cooled absolute alcohol were added. The mixture was shaken thoroughly and centrifuged at 12,000 g, RT for 20 min. Supernatant was discarded, and 75% ethanol 500 μl was added, then centrifuged at 12,000 RT for 5 min. Again the cDNA pellet was washed with 75% ethanol once, the liquid in the centrifuge tube was discarded, air dry, and the pellet was solved in RNAse-free water.

3) Synthesis of the Biotin-Labeled cRNA:

Biotin-labeled cRNA was prepared by Enzo® BioArray™ HighYield™ RNA transcript label kit (Enzo life sciences, INC). Above cDNA 5 μl was added with RNase-free water to 22 μl, and the following were added: 10×HY reaction buffer (Tube No. 1) 4 μl, 10× biotin-labeled nucleotide (Tube No. 2) 4 μl, 10×DTT (Tube no. 3) 4 μl, 10× RNase inhibitor mixed solution (Tube No. 4) 4 μl, 20×T7 polymerase (Tube No. 5) 2 μl. The mixture was mixed thoroughly, slightly centrifuged, and incubated at 37° C. for 4.5 h. Every 35 min, the mixture was centrifuged at 600 rpm for 10 s. The synthesis product can be stored at −20° C. or directly used in the next purification step.

Purification of cRNA. cRNA was purified with Qiagen kit. The method was substantially the same as for the total RNA (see steps 2-6).

Quantification and detection of cRNA. The cRNA concentration and the ratio of OD260/OD280 were detected by UV spectrophotometer, and the quality of cRNA was assayed by denatured gel. 2 μg cRNA was electrophoresized on 1.2% formaldehyde denatured gel, the purified cRNA visualized as diffuse strip (FIG. 1).

Fragmentation of cDNA. cRNA 30 μg was added with 5× fragmentation buffer 12 μl and RNAse-free water to 60 μl. Mixed thoroughly, incubated at 94° C. for 35 min, then placed on ice.

Figure 2:
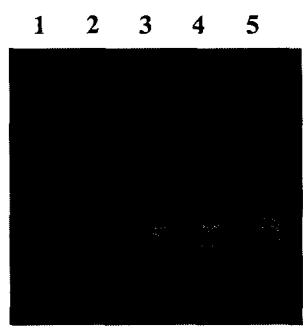
FIG. 2 indicates the electrophoresis map of the fragmented cRNA labeled by biotin. 1-5 are sample numbers.

Detection of fragmented cRNA: 2 μg cRNA was electrophoresized on 1.2% formaldehyde denatured agarose gel, the visualized fragments of cRNA were about 35-200 bp (FIG. 2).

4) Chip Hybridization:

The hybrid buffer was formulated. According to the chip type, suitable amount of hybrid buffer was formulated according to the following table. One sample chip needs 250 μl hybrid buffer, and one assay chip needs 90 μl hybrid buffer. The formulation is provided in Table 1.

TABLE 1

The formulation of chip hybrid buffer

| | Formulation | 600 μl | Final conc. |
|---|---|---|---|
| 1. | Fragmented cRNA (0.5 mg/ml) | 60 μl | 0.05 μg/μl |
| 2. | Oligo B2 control (3 nM) | 10 μl | 50 pM |
| 3. | 20× eukaryotic hybridization control | 30 μl | 1× |
| 4. | Salmon sperm (9.3 mg/ml) | 6.46 μl | 0.1 mg/ml |
| 5. | Acetylated BSA (20 mg/ml) | 15 μl | 0.5 mg/ml |
| 6. | 2× hybrid buffer | 300 μl | 1× |
| 7. | RNase-free water | 178.6 μl | |

According to the chip hybridization method provided by Affymetrix, the assay chips were first hybridized, washed and stained, and analyzed. Then, sample chips were hybridized and assayed according to the results of the assay chips. The procedure of the chip hybrid assay was simply described as follows with step 1 and 2 performed simultaneously until step 3 to finish.

Step 1: Pre-hybridization of the chips. The chips were taken out and balanced to RT. 1× hybrid buffer was added, and then pre-hybridized at 45° C., 60 rpm for 10 min.

Step 2. Preparation of the hybrid buffer. Hybrid buffer was mixed thoroughly and incubated at 99° C. for 5 min. Then it was shifted to 45° C. and incubated for 5 min. Then the mixture was centrifuged at maximum speed for 5 min.

Step 3. Hybridization of the chips. 1× hybrid buffer was aspired from the chips. The hybrid buffer was added into the chips, then hybridized at 45° C. 60 rom for 16 h. After hybridization, the hybrid buffer in the chips was aspired, then Wash A was added for the rinse and stain process.

5) Elution of the Chips.

Elution program was run on Eluting workstation according to the chip type and the Chip elution method provided by Affymetrix.

6) Scanning of the Chips.

According to the chip scan method provided by Affymetrix, chip was scanned on the scanner.

The human whole genome expressing chip of Affymetrix (Affymetrix, GeneChip® human genome U133 plus 2.0 arrays) includes $4.7 \times 10^4$ gene transcripts and the splice variants of about $3.85 \times 10^4$ genes of the human complete genome. The said chip was used to analyze the gene expression spectrum of the cancer tissue and non-cancerous liver tissue of the human liver cancer subjects, and it was found that DKK-1 gene was highly expressed in liver cancer, the expression in liver cancer tissue was about 30 times higher than non-cancerous liver tissue.

Example 4

Northern Hybridization

1) Preparation of Northern Film

Preparation. Electrophoresis chamber, gel plate and comb were dipped in 3% oxydol for more than 15 min, then rinsed clean by autoclaved DEPC processed water. Graduate and conical flask were dipped in DEPC water over night, 180° C. parched for 8 h. 10×MOPS formaldehyde gel electrophoresis buffer (Huashun, Cat W67) was used to formulate 1× formaldehyde gel electrophoresis buffer 1000 ml: 10×MOPS formaldehyde gel electrophoresis buffer 100 ml, 37% formaldehyde 20 ml, and Rnase-free water 880 ml. Formulation of 5×RNA load buffer: 80 µl 500 mM EDTA (pH8.0), 720 µl 37% formaldehyde, 2 ml 100% glycerol. 3084 µl formamide, and 4 ml 10×MOPS formaldehyde gel electrophoresis buffer. An amount of bromophenol blue was added, and RNAse-free water was added to make the volume up to 10 ml. The preparation of 1% formaldehyde gel denatured gen: 1 g agarose (GIBCO BRL, Cat 15510-027) was weighted and RNase-free water 90 ml was added. The agarose was microwave melted and then 1.8 ml 37% formaldehyde, 10 ml 10×MOPS formaldehyde gel electrophoresis buffer was added, thoroughly mixed and then filled into gel. Before the electrophoresis, the gel was hold in 1× formaldehyde gel electrophoresis buffer to balance at least 30 min. The denaturation of RNA samples: From each sample, total RNA 10 µg was taken, and 1 volume of 5×RNA load buffer was added for every 4 volumes of sample. The mixture was mixed thoroughly and then incubated at 65° C. for 10 min, and immediately put on ice.

The RNA sample after electrophoresis, transfer and denaturation was on formaldehyde gel denaturation electrophoresis for 4 h, using up-run capillary method to transfer the RNA on the gel to the nylon film (S&S, Cat 99J071). Load of 500 g was proposed, and the transfer time was 18-24 h. The film was taken out, and rinsed in Milli Q water for several minutes. The film was dried at 37° C., baked at 80° C. for 1.5 h, to immobilize the RNA on the nylon film.

2) Labeling and Purification of DNA Probes:

Preparation of the probes. DKK-1 gene was PCR amplified. Specific primer including its coding region was designed according to cDNA sequence of human DKK-1 gene on NCBI website (using primer designing software primer3.cgi v0.2a). Forward primer 5'GACCCAGGCTTGCAAAGT-GACGGT3' and reverse primer 5'AGGAGTTCACTG-CATTTGGATAGCTGG3'. DKK-1 was amplified using human placenta cDNA (BD Clontech) as template. PCR kit was BD Advantae™2 PCR kit (Cat 639206). The reaction system is as follows: 10× reaction buffer 1.25 µl, forward and reverse primers (10 µM) each 1 µl, human placenta cDNA templates 1 µl, Advantage 2 Polymerase 0.5 µl and sterilized water 7.75 µl. Total reaction volume was 12.5 µl. Temperature condition was: 94° C. 30 sec, 72° C. 3 min, 5 cycles; 94° C. 30 sec, 70° C. 30 sec, 72° C. 3 min, 5 cycles; 94° C. 30 sec, 68° C. 30 sec, 72° C. 3 min, 27 cycles. After reaction, 1% agarose gel electrophoresis was used to recover and purify the specific bands. PCR products were linked to TA clone, and then transformed into competent E. coli. TOP10$^F$. White colonies were picked and inoculated into LB medium, 37° C. overnight. Plasmid DNA was extracted, identified by PCR method and EcoRI (Promega, Cat R6011) enzyme cleavage. The positive clones including the inserted fragments were sequenced. The correct positive clones were sequenced, the plasmids were extracted, and cleaved by EcoRI. DKK-1 fragments were recovered by electrophoresis and stored at −20° C. for use as probes.

Labeling the probes: DNA probes were labeled by radioactive [α-$^{32}$P]dCTP (Amersham Biosciences, Cat PB10205) by random primer method as follows: 25 ng DKK-1 probe DNA was solved in RNase-free water (1-33 µl), left in boiled water for 5 min to denature the DNA, immediately left on ice for 5 min and refrigerated centrifuged immediately. Following reagents were added into the above DNA sample sequentially: 10× labeling buffer (including the random primers) 5 µl, dNTPs (dATP, dTTP, dGTP each 2 µl) 6 µl, [α-$^{32}$P]dCTP (3000 Ci/mmol, 50 µCi) 5 µl, DNA Polymerasel-klenow fragments (5 u) 1 µl. Incubated at 37° C. for 1 hr.

The labeled DNA probes were purified with QIAquick Nucleotide Removal kit (Qiagen, Cat 28304), according to the instruction provided by the company.

3) Hybridization:

The prepared films were wetted by Milli Q water, and put into 68° C. pre-heated hybridization buffer (BD Bioscience, Cat 636832) to pre-hybridize more than 3 hours. Salmon sperm DNA was added to 100 µg/ml.

The purified probes were heated in 95-100° C. water for 5 min, put on ice bath immediately for 5 min, and added into hybrid tubes, then hybridized at 68° C. for 18-24 h.

The films were washed to remove excess and non-specific hybridized probes. The solution for washing the films was Solution 1 (2×SSC, 0.05% SDS) and Solution 2 (0.5×SSC, 0.1% SDS).

4) Pressing the Film:

The films washed were closed in plastic films, then X ray films were pressed above and exposed at −70° C.

Figure 3:
FIG. 3 indicates the Northern hybridization expression analysis of DKK-1 gene in 12 liver cancer patients.
Figure 4:
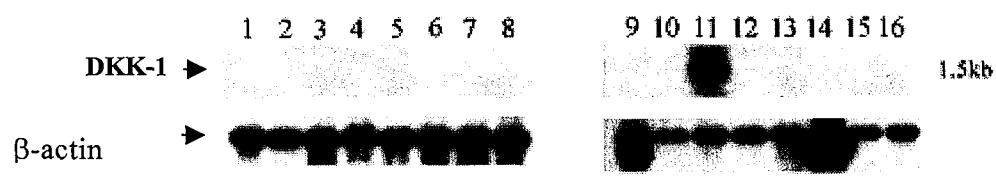
FIG. 4 indicates the analysis of DKK-1 gene expression in 16 normal human tissues. The numbers are respectively: 1. spleen, 2. thymus, 3. prostate; 4. testicle; 5. ovary; 6. small intestine; 7. large intestine; 8. peripheral blood lymphocyte; 9. heart; 10. brain; 11. placenta; 12. lung; 13. liver; 14. muscle; 15. kidney; 16. pancreas.

Northern hybridization assay was used to test the expression profiles of the cancer tissue and non-cancerous liver tissue of the 12 liver cancer patients, and it was found that 7 patients only highly expressed DKK-1 in cancer tissues, and the non-cancerous liver tissue in the same patient did not express DKK-1 (FIG. 3). The load amount of each sample was about 10 µg total RNA. Furthermore, in all the 16 normal tissues analyzed DKK-1 only expressed in placenta tissue, and in all the other 15 normal adult tissues it did not express (FIG. 4). Each normal human tissue included about 2 µg polyA$^+$ RNA.

Example 5

Elisa Assay for the DKK-1 Protein Amount in the Peripheral Blood of Liver Cancer Patients Coating the 96-well Elisa plate. 50 µl, goat anti-human DKK-1 polyclonal antibodies (R&D systems, Inc., Cat AF1096, 100 ng/µl) were solved in 4,950 µl PBS solution. Each well of the 96-well ELISA plate was added 50 µl the above dilution and 4° C. overnight. The wells were rinsed by 0.05% PBST solution 200 µl 3 times, each time 3 min.

Each well was added 100 µl PBS with 4% BSA (Sigma, Cat A3059-50G), block at RT for 2 h, then rinsed with 200 µl 0.05% PBST 3 times, each time 3 min.

10 µl serum was added into 90 µl PBS supplemented with 0.1% Tween and 1% BSA. Each sample was added duplicated, each well 50 µl. 2 µl recombinant human DKK-1 protein standard (R&D systems, Inc., Cat 1096-DK, 10 ng/µl) was added into 400 µl PBS supplemented with 0.1% BSA, and then diluted by fold. 7 dilution degrees were set, each standard was added in duplicate and each well was added 50

μl. The plate was incubated at RT for 2 h, and then rinsed with 200 μl 0.05% PBS for 3 times, each time 3 min.

20 μl biotin labeled goat anti-human DKK-1 antibody (R&D systems, Inc., Cat. BAF1144, 50 ng/μl) was diluted in 4,980 μl 0.1% BSA in TBS, each well was added 50 μl the above dilution. The plate was left at RT for 2 h, then rinsed with 200 μl 0.05% PBS for 3 times, each time 3 min.

0.5 μl Horseradish peroxidase conjugated with streptavidin (Vector laboratories, Inc., Cat. SA-5004) was diluted into 5 ml buffer (10 mM phosphate, 0.15 M NaCl, 0.1% Tween 20, pH 7.8), and 50 μl above dilution was added into each well, incubated at RT for 30 min. The wells were rinsed by 200 μl 0.05% PBST for 3 times, each time 3 min.

100 μl OPD substrate solution [8 mg OPD (DakoCytomation, Cat. S2045) solved in 12 ml water and 5 μl $H_2O_2$] was added into each well to develop, incubated RT for 30 min.

100 μl 0.5M $H_2SO_4$ terminate buffer was added into each well, and the wells without standards were used as blank control. The OD of each well were tested at 490 nm.

Log-log standard curve was plotted according to the standards (logOD versus logCONCENTRATION), and then DKK-1 amount in each serum sample was calculated.

ELISA results of the serum DKK-1 of liver cancer patients as follow: The average value of DKK-1 in 34 normal human serums is about 3.61 μg/L (with the maximum of 8.21 μg/L). Average value in 14 cirrhosis patients is about 2.93 μg/L (with the maximum of 10.73 μg/L). The average value of 128 liver cancer patients is about 4.85 μg/L [wherein 10 are 10 μg/L<DKK-1<20 μg/L; 1 DKK-1=144.4 μg/L. 11/128 make up to 8.59% of the total liver cancer patients tested. In the 11 patients with high DKK-1, 2 are AFP negative liver cancer patients, and 1 is AFP<200 μg/L liver cancer patient (AFP=60.15 μg/L), making up to 27.3% (3/11)].

Example 6

ELISA Assay and Analysis of DKK-1 Secreted by Multiple Kinds of in Vitro Cultivated Human Tumor Cells 35 mm petri-dish was used to anabiosis the cells. Cell was passed into 35 mm dish when growing into 90% confluence. About $3 \times 10^5$ cells and 1 ml medium were added into each dish. 24 h later cell culture supernatant was collected.

The coating conditions and method of the 96-well ELISA plate were completely the same as in Example 5. 20 μl cell culture supernatant was added into 80 μl PBS supplemented with 0.1% Tween and 1% BSA. Each sample was added in duplicate, each well 50 μl. The rest experiment was operated completely according to Example 5.

In the control of calf serum complete medium and fetus bovine serum complete medium, the concentration of DKK-1 protein was substantially 0 (Table 2). In the culture supernatants of control murine fibroblast NIH3T3 and murine normal liver fibroid cell HSC-T6, DKK-1 protein was not detected, either (Table 2). However, highly expressing DKK-1 protein was found in 8 human tumor cell or human embryonic kidney cell 293, wherein human cerebral glioma cell U251 is the highest (214.6 μg/ml) (Table 2).

TABLE 2

Assay of DKK-1 protein amount in the tumor cells culture supernatant

| Cell type | DKK-1 amount in the cell culture supernatant |
|---|---|
| Calf serum complete medium control | 0.0 |
| Fetus bovine serum complete medium control | 1.8 |
| Murine fibroblast NIH3T3 | 0.8 |
| Murine normal liver fibroid cell HSC-T6 | 0.5 |
| Large cell lung cancer A549 | 143.1 |
| Ovarian cancer SKV03 | 15.5 |
| Gastric cancer SW-1900 | 51.0 |
| Breast cancer MCF-7 | 69.5 |
| human embryonic kidney cell 293 | 51.9 |
| Rat cerebral glioma C6 | 55.4 |
| Human cerebral glioma U251 | 214.6 |
| Cervic cancer C33A | 85.2 |
| Cervic cancer HeLa | 102.3 |
| melanoma A375 | 74.8 |
| Highly metastatic melanoma SCI-375 | 61.1 |
| Low metastatic hepatoma cell MHCC97-L | 112.0 |
| Highly metastatic hepatoma cell HCCLM3 | 118.2 |
| hepatoma cell HepG2 | 182.8 |
| hepatoma cell Hep3B | 58.7 |
| hepatoma cell BEL-7402 | 79.1 |
| hepatoma cell SMMC-7721 | 52.3 |
| hepatoma cell HuH7 | 76.7 |

Example 7

Kit

A kit was prepared which comprised nucleic acid probes directed at DKK-1 (prepared as in Example 4), PCR reaction buffers (for amplify DKK-1). According to standard protocol, cDNA from normal tissues and cancer cells of 100 hepatoma patients were amplified. The detection results showed that the expression amount of DKK-1 in hepatoma cells of the 100 hepatoma patient was 100 times of the normal cell.

For the same reason, patients with lung cancer, breast cancer and glioma were also detected. Same results with DKK-1 expression as 50-100 times high were also obtained.

Example 8

A kit was used according to the method of Example 5, which comprised specific antibodies against DKK-1 (prepared as in Example 5) and ELISA reagents. According to standard protocol, ELISA assay was done for normal tissues and cancer cells of 100 hepatoma patients. The detection results showed that the expression amount of DKK-1 in hepatoma cells of the 100 hepatoma patient was 100 times of the normal cell.

For the same reason, patients with lung cancer, breast cancer and glioma were also detected. Same results with DKK-1 expression as 50-100 times high were also obtained.

Example 9

Radioimmunoimaging and biological distribution research was done on nude mouse model with human hepatoma using DKK-1 specific monoclonal antibody.

1. Material and Method 1.1 11 4-6 weeks old about 20 g male BALB/C nude mice were grown in Shanghai Cancer Institute. Anti-DKK-1 monoclonal antibody 500 μg/1 ml, mIgG1 antibody 1 mg/1 ml, available from R&D systems, Inc.

1.2 Cultivation of the Cells.

(1) Cell resuscitation: Frozen human hepatoma SMMC-7721 cell cryovial was taken out, and fast cast into 37° C. bath to recover the temperature and melted fast. (2) The cry vial was taken out of the bath and opened. Cell suspension was aspired with pipette, filled into centrifuge tube and 5 ml culture medium (DMEM+10% calf serum) was added dropwise. After mixing, centrifuged at 1000 rpm for 5 min, and the supernatant was removed. Rinsed for 3 times. (3) After rinsing, the cells were diluted with culture medium, inoculated into culture flask, in which 5 ml culture medium was added, and then put in 37° C. $CO_2$ incubator. On next day, the culture medium was changed and the incubation continued. (4) When the adherent cell were up to 80%, they were digested and divided several flasks. The culture medium was aspired completely with pipette, and the culture was washed with PBS twice, and the PBS medium was aspired. Several drops of trypsin were added, mixed thoroughly, and kept flat in 37° C. incubator for digesting 1 min. Under inverted microscope it could be seen that the cells shrinked into round shape. 2 ml culture medium was added to stop the digestion, and the cells were removed from the flask wall, and moved into clean tubes, 1000 rpm for 5 min. Supernatant was removed, 2 ml culture medium was added to resuspend the cell pellet, mixed thoroughly. (5) Cells were counted and average value was calculated.

1.3 Establishing of the Nude Mice Model with Human Hepatoma

SMMC-7721 cell were prepared with PBS into unicell suspension. 4 nude mice were each subcutaneously injected at the back SMMC-7721 cell $0.2$-$1\times10^7/0.2$ ml. When the tumor grew up to about diameter 0.8 cm, it was removed by surgery. The tumor was immediately immersed into sterile physiological saline, and cut into small parts of 2.0 mm diameter, then transplanted subcutaneously in the right side of the back of the nude mouse with trocar. Such transplant were repeated several times (each time not more than 3 nude mice) to make the in vivo biological properties of SMMC-7721 cell stable. 11 nude mice were selected to transplant subcutaneously in the right side of the back using above procedure. After 5 weeks, the tumors grew into 1 cm in diameter for use.

1.4 Labeling anti-DKK-1 monoclonal antibody using modified chloramine T method, using iodine [$^{131}$I] to mark anti-DKK1 monoclonal antibody and IgG1, isolated and purified on Sephadex G50 column. The radioactive chemical purity of iodine [$^{131}$I] was tested as 95%, radioactive concentration was 200 μCi/ml, radioactive specific activity was 5 μCi/μg. The radioactive chemical purity of iodine [$^{131}$I]-IgG1 was tested as 94%, radioactive concentration was 75 μCi/ml, and radioactive specific activity was 1 μCi/μg 1.5 24 h before assay, the mice were fed 1% KI water to block thyroid. The detailed experimental steps were as follows: (1) Assay group and the administration protocol: nude mice were divided into A and B groups, each group having 6 and 5 nude mices. Group A were all injected at vena caudalis with 30 μCi iodine [$^{131}$I]-DKK1 and group B were all injected at vena caudalis with 12 μCi iodine [$^{131}$I]-IgG1. (2) Biological distribution and visualization: SPET visualization. Mice were anaesthetized by inhaling of ether after 24, 48, 96 and 120 hours after injection of labeled antibodies, fastened by adhesive plaster and ran SPECT. ADAC WeltesPlus double sensor SPECT was used, which equipped high energy collimator, energy peak 364 Kev±10% window width, matrix 64×64, magnification 2.02, preset collection count 100K. (3) After SPECT 24, 48, 96, 120 h, mice were executed by pulling neck and tumor, blood, liver, lung and other organs were collected, weighted and counted for radioactivity.

Figure 5:
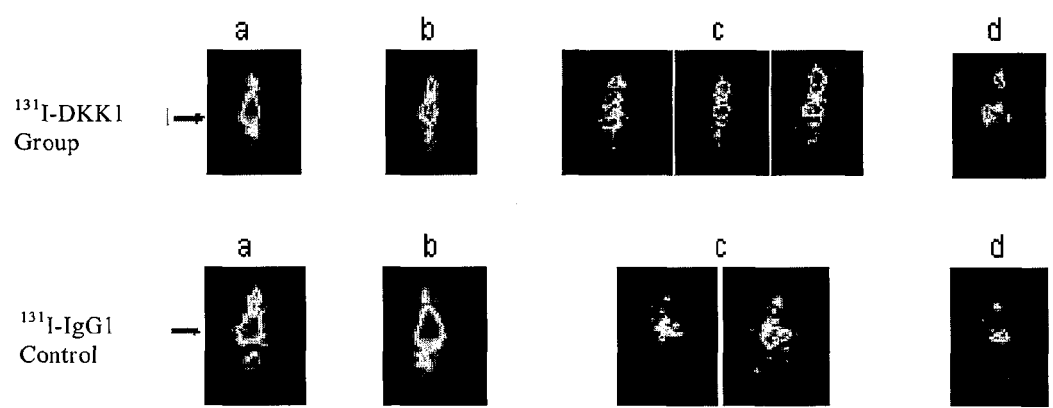
FIG. 5 is the radioactive immunoassay result of mice, wherein (a) is 24 hours' display result; (b) is 48 hours' display result; (c) is 96 hours' display result; (d) is 120 hours' display result.

2. Result 2.1 SPECT results: 1 in 6 experimental mice in Group I had positive image (See FIG. 5). Experimental group II did not have positive image. Group I evidently was advantageous than group II.

Figure 6:
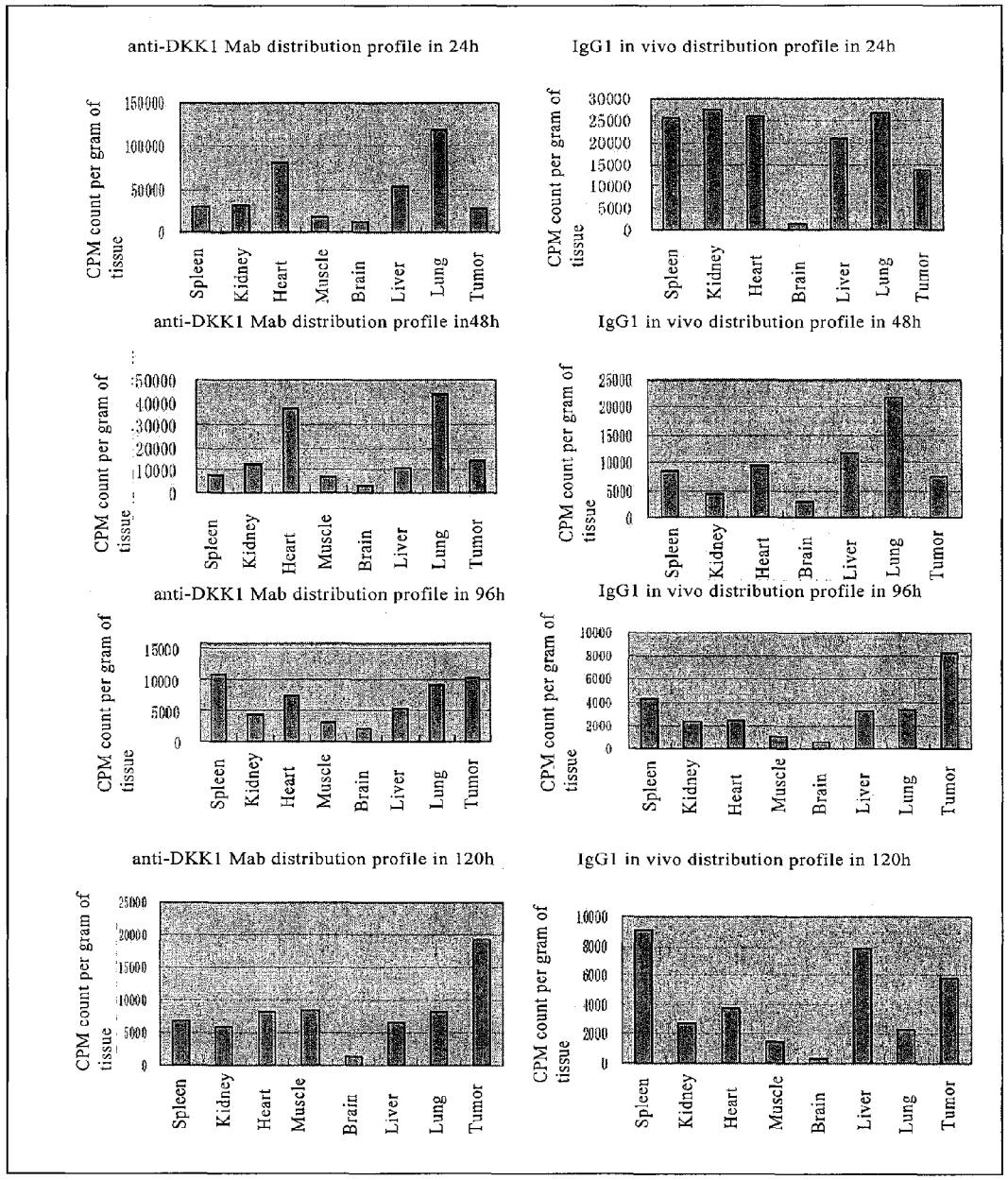
FIG. 6 is $^{131}$I-DKK1 distributing profile. As shown in the figure, $^{131}$I-DKK1 gathers in the tumor tissue as time passes, and reaches the peak at 120 hour. $^{131}$I-DKK1 reaches the peak in mice at 96 hour.

2.2 $^{131}$I-DKK1 distribution profile (See FIG. 6) showed that $^{131}$I-DKK1 gathered in the tumor tissue as time passed, and reached the peak at 120 h. $^{131}$I-IgG1 in mice reached peak at 96 h.

3. Discussion

The characters of nuclide tumor imaging, such as high specificity, high sensitivity, non-traumatic and systematic make it the preferred screening examination for certain diseases and it is effective staging tool before certain tumor therapies. The present experiment used in vivo distribution experiment with $^{131}$I labeled anti-DKK1 monoclonal antibodies, and demonstrated that after injection of anti-DKK1 monoclonal antibody the tumor area has apparent radioactivity gathering, which indicates that anti-DKK1 monoclonal antibody can recognize the tumor and the normal tissue, and has high affinity to human hepatoma cells.

All above-noted published references are incorporated herein by reference as individual reference is incorporated. Furthermore, it should understand that the skilled in the art can modify and verify the present invention in light of the above disclosure of the present invention. Such equivalents are also encompassed in the scope of the claims appended hereto.

The invention claimed is:

1. A method to detect cancer in a subject, wherein the cancer is selected from liver cancer, lung cancer, breast cancer and glioma, comprising:

applying to a sample obtained from a subject an anti-DKK-1 specific antibody or a DKK-1 protein specific nucleic acid probe, wherein the anti-DKK-1 specific antibody binds to DKK-1 protein, wherein the DKK-1 protein specific nucleic acid probe binds to a nucleic acid sequence that encodes the DKK-1 protein, and wherein each of the DKK-1 protein and the nucleic acid sequence that encodes the DKK-1 protein is a molecular marker for the cancer;

measuring an amount of the DKK-1 protein or the nucleic acid sequence that encodes the DKK-1 protein by measuring an amount of a first signal generated by a first labeling substance that is conjugated to the anti-DKK-1 specific antibody or an amount of a second signal generated by a second labeling substance that is conjugated to the DKK-1 protein specific nucleic acid probe; and comparing the amount of the DKK-1 protein or the nucleic acid sequence that encodes the DKK-1 protein in the sample with an amount of the DKK-1 protein or the nucleic acid sequence that encodes the DKK-1 protein in a normal control, wherein an increase in the amount of the DKK-1 protein or the nucleic acid sequence that encodes the DKK-1 protein in the sample as compared to the amount of the DKK-1 protein or the nucleic acid sequence that encodes the DKK-1 protein in the normal control indicates that the subject has the cancer.

2. The method of claim 1, wherein the anti-DKK-1 specific antibody is linked to a radionuclide.

3. The method of claim 1, wherein the anti-DKK-1 specific antibody is a monoclonal antibody or a polyclonal antibody.

4. The method of claim 1, wherein the cancer is liver cancer.

5. The method according to claim 1, wherein the subject is human.

6. The method according to claim 2, wherein the radionuclide is $^{133}$I.

7. The method of claim 1, wherein the sample is a body fluid sample.

8. The method of claim 7, wherein the body fluid sample is a blood sample.

* * * * *